June 13, 1950 L. MORO Plant Pat. 951
ROSE PLANT
Filed May 20, 1949
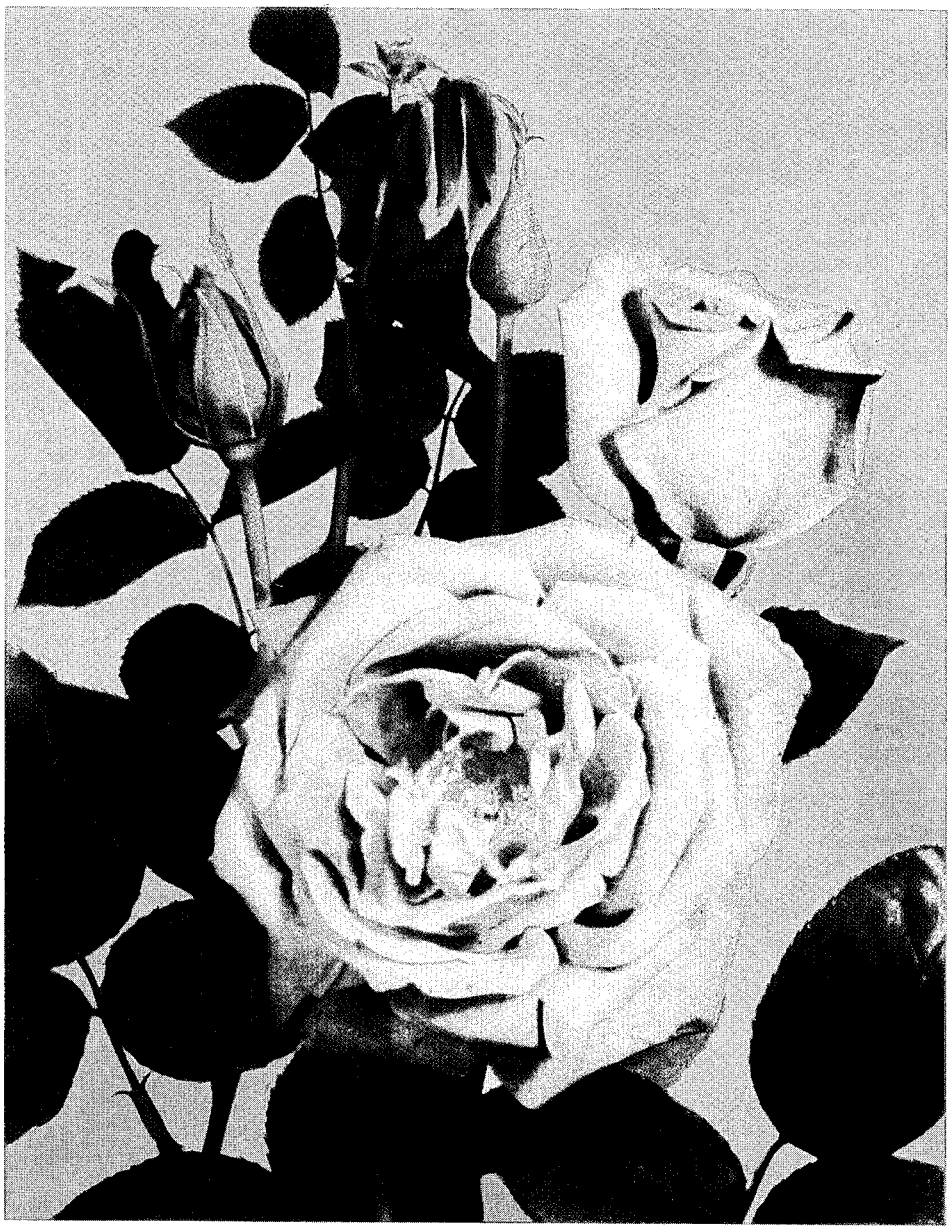
Inventor
L. Moro
By Robb & Robb
Attorneys Patented June 13, 1950

Plant Pat. 951

UNITED STATES PATENT OFFICE

951

ROSE PLANT

Luciano Moro, Hartebeespoort, Transvaal, Union of South Africa, assignor to Jackson & Perkins Company, Newark, N. Y., a corporation of New York Application May 20, 1949, Serial No. 94,433

1 Claim. (Cl. 47—61)

The present invention relates to a new and distinct variety of Rose plant of the hybrid tea class, and is characterized as to novelty by its large size of bloom borne on a long, strong stem, which makes it exceptionally desirable for cut flower purposes; by the retention of the color of the bloom through the period much desired in such cut flowers; and by the well shaped bush suitable for outdoor use and the great productivity of bloom thereon.

In the accompanying drawing specimens of the blooms of this new variety on a reduced scale are shown at different stages of development clearly disclosing the substantially uniform rose red coloring retained throughout these stages, this coloring being a distinguishing feature of novelty.

The following is a detailed description of the new variety, color terminology being in accordance with Ridgway's Color Standards and Nomenclature:

Parentage: Seedling.
- *Seed parent.*—"Charles P. Kilham" (unpatented).
- *Pollen parent.*—"Rome Glory" (Pl. Pat. No. 304).

Classification: Botanic and commercial—hybrid tea.

Place where asexually reproduced.—Newark, New York.

Method of reproduction.—Budding.

*Flower*

(The following observations made in greenhouse at Newark, New York, in the afternoon in the month of November.)

Blooming Habit: Recurrent—continuous.

Bud:
- *Size.*—Very large.
- *Form.*—Long; pointed. Is not affected by wet or hot weather.
- *Color.*—When sepals first divide—Pomegranate Purple, Plate 12. When petals begin to unfurl—between Pomegranate Purple Plate 12, and Rose Red, Plate 12. When half blown—inside of petals—Tyrian Rose, Plate 12, overcast with Rose Red, Plate 12; reverse of petals—Rose Red, Plate 12, overcast with Rose Color, Plate 12.
- *Sepals.*—Serrated, branched, "hood" above bud. Curl back when petals begin to unfurl. Color — inside — Chrysolite Green, Plate 31; outside—Absinthe Green, Plate 31.

- *Calyx.*—Shape—funnel. Size — large. Aspect—smooth. Odor when rubbed—none. Color—Apple Green, Plate 17.
- *Peduncle.*—Length—Long. Aspect—prickly. Color—Parrot Green, Plate 6. Strength—stiff; heavy.
- *Opening.*—Opens up well. Is not affected by adverse weather conditions.

Bloom:
- *Size.*—Very large. Average size when fully expanded, 6"–6½".
- *Borne.*—Singly and several.
- *Stems.*—Long; strong.
- *Form.*—When first open—cupped. Permanence—retains its form to the end.
- *Petalage.*—Double (full but open center). Number of petals under normal conditions, 25.
- *Color.*—Center of flower—Rose Red, Plate 12. Outer petals—Rose Red, Plate 12, overcast with Rose Color, Plate 12. Base of petals (aiglet) — Light Greenish Yellow, Plate 5. Inside of petals—Tyrian Rose, Plate 12. Reverse of petals—between Rose Color, Plate 12, and Rose Red, Plate 12. General tonality from a distance—Tyrian Rose, Plate 12.
- *Discoloration.*—General tonality at end of first day — Rose Red, Plate 12. Second day—Tyrian Rose, Plate 12. Third day—Tyrian Rose, Plate 12, overcast with Rose Color, Plate 12.

Petals:
- *Texture.*—Thick. Is not affected by wet or hot weather.
- *Appearance.* — Inside — velvety; outside — satiny.
- *Form.*—Oval.
- *Arrangement.*—Informal (with "rags" in center). Petaloids in center—few; large.
- *Persistence.*—Drop off cleanly.
- *Fragrance.*—Slight. Nature — fruity (Russet apple).
- *Lasting quality.*—On the plant and as cut flower—long.

Genital organs:
- *Stamens, anthers.* — Medium size; many. Color—Orange Buff, Plate 3. Arrangement—regular around styles.
- *Stamens, filaments (threads).*—Long. Color —Mikado Orange, Plate 3.
- *Pollen.*—Color—Capucine Buff, Plate 3.
- *Styles.*—Bunched uneven length; medium length; thin.
- *Stigmas.*—Color—Baryta Yellow, Plate 4.

*Ovaries.*—All enclosed in calyx, some protruding from calyx.

*Plant*

Form: Bush.
Growth: Vigorous; upright.
Foliage: 5 to 7 leaflets.
*Size.*—Large.
*Quantity.*—Abundant.
*Color.*—New foliage: upper side—Yellowish Oil Green, Plate 5; serrations, Oxblood Red, Plate 1; under side—Oil Green, Plate 5, overcast with Oxblood Red, Plate 1. Old foliage: upper side—Elm Green, Plate 17; under side—Light Bice Green, Plate 17.
*Shape.*—Oval pointed.
*Texture.*—Upper side—leathery. Under side—smooth. Ribs and veins—ordinary.
*Edge.*—Serrated (saw toothed).
*Serration.*—Single; small.
*Leaf stem.*—Color—Courge Green, Plate 17. Under side—smooth.
*Stipules.*—Medium length; smooth.
*Disease resistance.*—Resistant.
Wood:
*New wood.*—Color—Claret Brown, Plate 1. Bark—smooth.
*Old wood.*—Color—Cress Green, Plate 1. Bark—smooth.
Thorns:
*Thorns.*—Quantity—on main stalks from base and on laterals from stalk—ordinary. Form—narrow base; medium length; hooked downward. Color when young—Eugenia Red, Plate 13. Position—irregular.
*Prickles.*—On main stalks and on laterals—few. Color—Yellowish Oil Green, Plate 5.
*Short needles.*—On main stalks and on laterals—none.

It will be apparent from the foregoing that this new variety rose resembles both of its parents, but is predominantly like "Rome Glory." However, the flower petals are larger and not quite so symmetrical as in "Rome Glory," having taken this characteristic from its seed parent. The foliage also is slightly like that of the seed parent.

I claim:

A new and distinct variety of rose plant characterized as to novelty by the large size of its blooms and the long strong stems bearing the same, suitable for cut flowers, the retention of the color of the blooms throughout the blooming period when they are usable as cut flowers, the great productivity of bloom and the well shaped bush for outdoor use, substantially as shown and described.

LUCIANO MORO.

No references cited.